United States Patent
Schulze et al.

(10) Patent No.: US 7,223,239 B2
(45) Date of Patent: May 29, 2007

(54) MEDICAL DEVICE THAT REMOVABLY ATTACHES TO A BODILY ORGAN

(75) Inventors: Dale R. Schulze, Cincinnati, OH (US); Christopher J Hess, Lebanon, OH (US); Michael F. Clem, Lebanon, OH (US); Gary W. Knight, West Chester, OH (US); Kevin A. Harper, Mason, OH (US); Rudolph H Nobis, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/032,288

(22) Filed: Jan. 10, 2005

(65) Prior Publication Data

US 2005/0148856 A1  Jul. 7, 2005

Related U.S. Application Data

(62) Division of application No. 10/104,606, filed on Mar. 22, 2002, now abandoned.

(51) Int. Cl.
*A61B 5/05* (2006.01)
*A61N 7/00* (2006.01)

(52) U.S. Cl. .......................................... 600/439; 601/2

(58) Field of Classification Search ............... 600/439, 600/459, 462, 471; 601/2, 7; 607/115, 116, 607/119, 126, 128
See application file for complete search history.

(56) References Cited

U.S. PATENT DOCUMENTS

| | | | |
|---|---|---|---|
| 3,643,653 A * | 2/1972 | Takahashi et al. | 600/129 |
| 4,047,532 A | 9/1977 | Phillips et al. | |
| 4,844,081 A * | 7/1989 | Northeved et al. | 600/439 |
| 5,095,907 A * | 3/1992 | Kudo et al. | 600/439 |
| 5,402,792 A | 4/1995 | Kimura | |
| 5,727,569 A | 3/1998 | Benetti et al. | |
| 5,772,675 A | 6/1998 | Hellenkamp | |
| 5,897,495 A | 4/1999 | Aida et al. | |
| 5,957,919 A | 9/1999 | Laufer | |
| 6,007,499 A | 12/1999 | Martin et al. | |
| 6,042,539 A | 3/2000 | Harper et al. | |
| 6,042,594 A | 3/2000 | Hellenkamp | |

(Continued)

FOREIGN PATENT DOCUMENTS

DE 35 44 628 A 6/1987

(Continued)

OTHER PUBLICATIONS

US 6,254,528, 07/2001, Khoui (withdrawn)

*Primary Examiner*—John P Leubecker

(57) ABSTRACT

A medical device for use on a bodily organ includes a concave support element that is removably attachable to the surface of the bodily organ, thereby defining an enclosed space adjacent to the bodily organ. The enclosed space is fluidly connected to a fluid management system for circulating a fluid inside of the enclosed space. The medical device also has an energy transfer element mounted to the concave support element and electrically connected to a control unit. In some embodiments, the energy transfer element transmits intense ultrasound energy in a frequency range of 1–30 megahertz, and the fluid acoustically couples the energy transfer element to the bodily organ, and the fluid also cools the energy transfer element.

6 Claims, 9 Drawing Sheets

U.S. PATENT DOCUMENTS

| | | | |
|---|---|---|---|
| 6,143,010 A | 11/2000 | Silvestrini et al. | |
| 6,176,855 B1 | 1/2001 | Heckele et al. | |
| 6,231,585 B1 | 5/2001 | Takahashi et al. | |
| 6,251,065 B1 | 6/2001 | Kochamba et al. | |
| 6,254,595 B1 | 7/2001 | Juhasz et al. | |
| 6,277,052 B1 | 8/2001 | Howard | |
| 6,280,415 B1 | 8/2001 | Johnson | |
| 6,626,855 B1 * | 9/2003 | Weng et al. | 601/3 |
| 6,645,202 B1 * | 11/2003 | Pless et al. | 606/41 |
| 6,773,408 B1 * | 8/2004 | Acker et al. | 601/2 |
| 2002/0002372 A1 | 1/2002 | Jahns et al. | |
| 2004/0073206 A1 | 4/2004 | Foley et al. | |

FOREIGN PATENT DOCUMENTS

| | | |
|---|---|---|
| WO | WO 99 34870 A | 7/1999 |
| WO | WO 01 05306 A | 1/2001 |
| WO | WO 02 11634 A | 2/2002 |
| WO | WO 02 15803 A | 2/2002 |

* cited by examiner

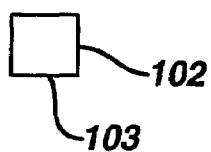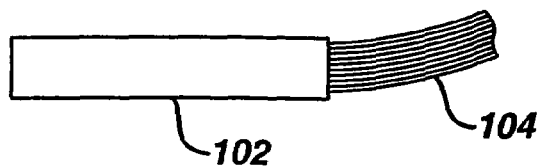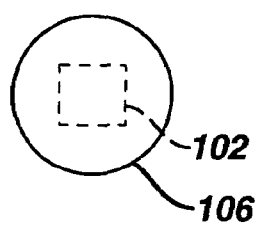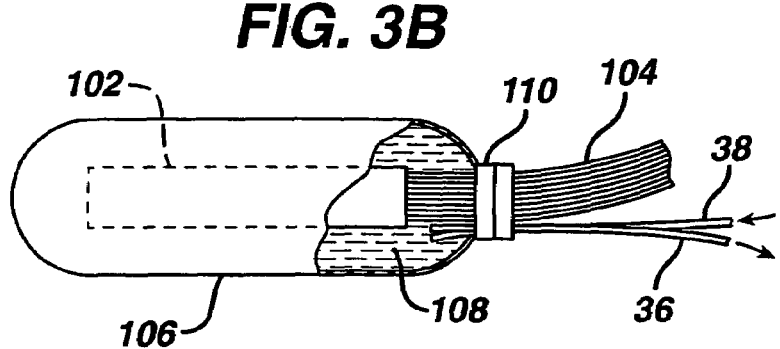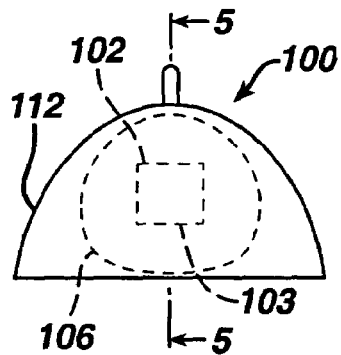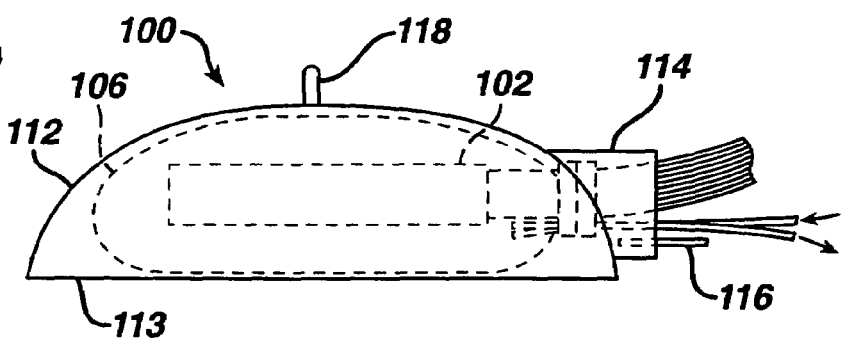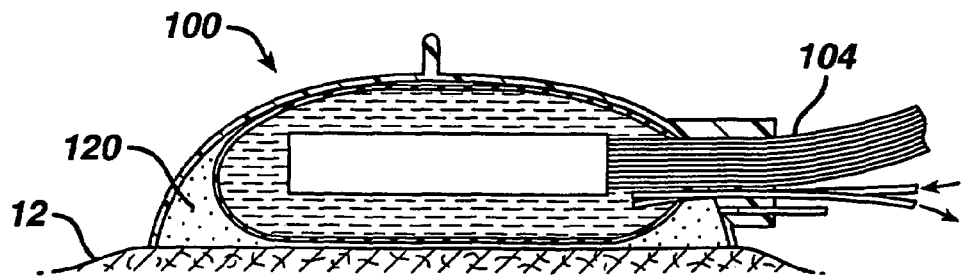

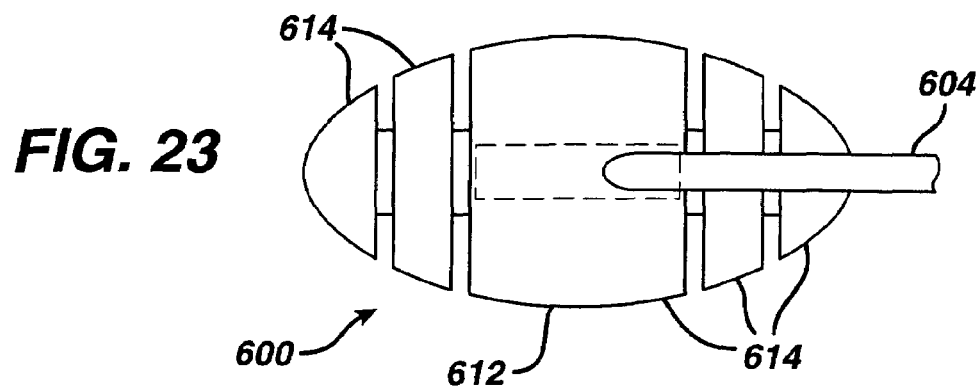
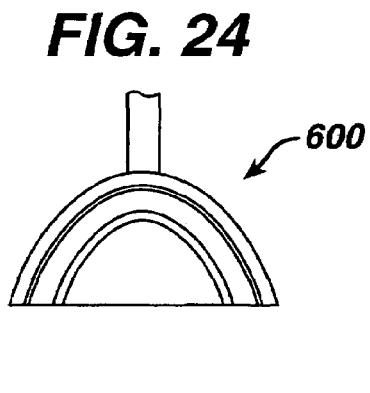
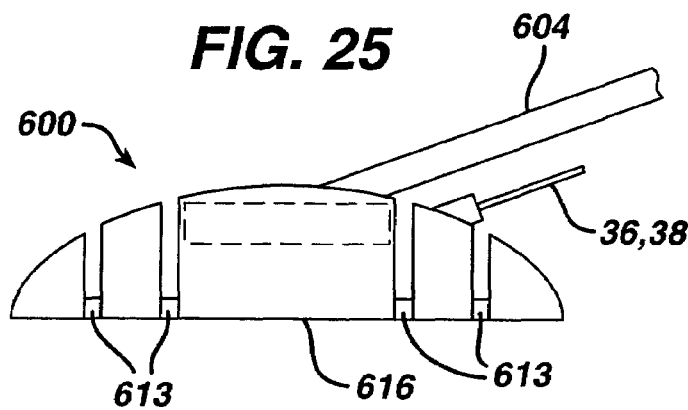
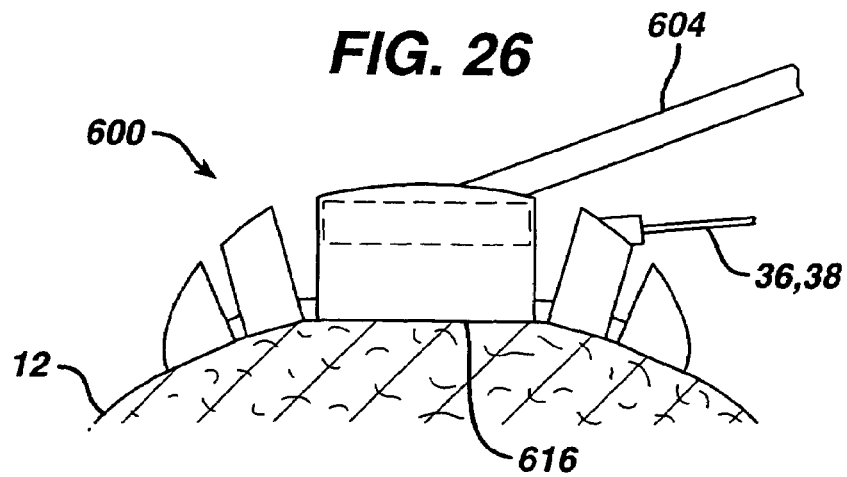

MEDICAL DEVICE THAT REMOVABLY ATTACHES TO A BODILY ORGAN

RELATED APPLICATIONS

This application Is a divisional of U.S. patent application Ser. No. 10/104,606, filed on Mar. 22, 2002, now abandoned, the disclosure of which is incorporated herein by reference.

FIELD OF THE INVENTION

The present invention relates, in general, to a medical device that removably attaches to a bodily organ and, more particularly, to such a medical device that transmits energy to tissue in or near the bodily organ.

BACKGROUND

Physicians have been treating cancerous liver tumors that are up to about five centimeters in diameter using numerous methods including electrosurgery, cryosurgery, and ethanol injection. Another option for treating liver tumors is the application of intense ultrasound energy (IUS). Investigators have been developing IUS devices and methods for several years, especially for treating diseased tissue in the prostate gland and liver. The frequency regime for IUS devices is generally in the range of 1–30 MHz. An inherent challenge when using IUS is maintaining a focused beam of acoustic energy from the ultrasonic energy transfer element onto the diseased tissue for a sufficient number of seconds to raise the temperature of the tissue high enough (at least 43 degrees C.) to cause tissue necrosis. It is then necessary to move the focus of the beam, which may be the size of a grain of rice, to a new, adjacent location to continue the ablation process. These steps are repeated until the entire volume of diseased tissue has been ablated. The time required to effectively treat this volume of tissue with IUS may exceed 20–30 minutes. It is critical, therefore, that the relative movement between the IUS energy transfer element and the tissue being treated is small to ablate selectively the tumor and a desired margin of healthy tissue in minimal time. During procedures for destroying diseased tissue within the liver, the physician must contend with movement of the liver due to the patient's breathing and the heart beating. When the diseased tissue is a cancerous tumor, it is obviously critical that as much of the cancerous cells as possible be destroyed to achieve the maximal therapeutic effect and to lengthen the patient's life.

Methods for stabilizing organs or for compensating for organ movement during medical procedures are well known in the art. For example, stabilization devices and methods developed for beating heart surgery include compression and/or vacuum attachment to immobilize a portion of heart while suturing together blood vessels. Enclosed platforms or dome-like structures for creating a workspace for endoscopic access and visualization have also been devised for vein harvesting and cardiac surgery. In addition, electrodes that attach to the skin of the patient for diagnoses or therapy of underlying tissue are also well known. These include electromyography (EMG) electrodes for monitoring muscular activity or functional electrical stimulation (FES) electrodes for stimulating muscular contraction. These electrodes move freely with the movements of the patient, thus minimizing relative movement between the electrode and the relevant tissue.

External, non-invasive IUS instruments developed for liver treatment require sufficient energy to offset losses of energy through the abdominal wall and to compensate for the movement of the liver. An alternate approach is to introduce a therapeutic IUS energy transfer element through a small incision in the abdomen and to attach it directly to the surface of the liver, and allow the energy transfer element to "ride" with the movement of the liver during the treatment. For example, a physician would position the IUS treatment energy transfer element on the anterior surface of the liver near a tumor with the aid of an intracorporeal, ultrasonic imaging device. The same imaging device would provide monitoring data to a control system in order to develop a "tool path" program for the energy beam focus. Then using electronic and mechanical focusing/directioning means, the IUS treatment energy transfer element would automatically ablate the tumor as the physician monitored the progress displayed on the control system.

Sometimes it is necessary to position the IUS energy transfer element apart from the organ surface so that the underlying tissue to be treated is in the focal range of the energy transfer element. Therefore, the IUS energy transfer element may be enveloped in a fluidic media such as, for example, a saline solution, having relatively the same acoustic energy transmission characteristics as the underlying tissue to provide acoustic coupling between the energy transfer element and the tissue. Also the IUS energy transfer elements generate a significant amount of heat. Since the efficiency of the IUS energy transfer element may decrease rapidly with temperature increase, the fluidic media also serves as a coolant for the energy transfer element. Devices having a water-filled balloon attached over the IUS energy transfer element, and maintained with a fresh water flow, have been effectively devised primarily for these purposes.

A multi-element, linear array IUS energy transfer element transmits acoustic energy from the energy transfer element face in an approximately two-dimensional plane, focusing at some distance away from the energy transfer element face. The focal depth and angular directivity within that plane of the focus may be set by the type of acoustic lens attached to the face of the energy transfer element, or electronically controlled within certain ranges. It may also be necessary, however, to physically move the energy transfer element to position the acoustic focus. For example, the energy transfer element may be rotated on its longitudinal axis to sweep the acoustic plane through a volume sector. It may also be vertically adjusted closer or nearer to the tissue.

What is needed, therefore, is a medical device that attaches directly to an internal bodily organ and moves freely with the movement of the organ in order to minimize the relative motion between the energy transfer element and the organ during treatment of underlying tissue. What is further needed is such a medical device that also incorporates energy transfer element coupling, cooling, and orienting/positioning means. What is further needed is also such a medical device that may be used minimally invasively on a surgical patient. The present invention addresses these needs and overcomes numerous deficiencies of the prior art.

SUMMARY OF THE INVENTION

The present invention is a medical device for use on a bodily organ of a patient that enables diagnostic or therapeutic instrumentation to be securely positioned relative to the bodily organ. The medical device generally comprises a concave support element, wherein the open side is removably attachable to the surface of the bodily organ, thereby defining an enclosed space adjacent to the bodily organ. The enclosed space is fluidly connected to a fluid management system for circulating a fluid inside of the enclosed space. The medical device also has an energy transfer element mounted to the concave support element. The energy transfer element is positioned and oriented for transmitting energy to the bodily organ. The medical device includes a cable for electrically connecting the energy transfer element to a control unit. Preferably, the energy transfer element transmits intense ultrasound energy in a frequency range of 1–30 megahertz. The fluid acoustically couples the energy transfer element to the bodily organ, and the fluid also cools the energy transfer element. Although the description of the invention will be discussed relating specifically to ultrasound energy, it will be appreciated by those knowledgeable in the art that various energy platforms may be used, such as, by example only, RF, microwave and laser.

In at least one embodiment, the fluid management system includes a vacuum source for adjustably creating an operating pressure within the enclosed space that is lower than the pressure external to the concave support element, for removably attaching the concave support element to the bodily organ.

In at least one embodiment, the medical device has an annular chamber circumventing the open side of the concave support element. The annular chamber is fluidly connected to a vacuum source for removably attaching the medical device to the bodily organ.

In another embodiment, the medical device has a plurality of hooking elements mounted on the concave support element. The hooking elements are remotely operable for removably attaching the concave support element to the bodily organ.

In at least one embodiment, the medical device also includes remotely controllable positioning means for adjusting the position of the energy transfer element with respect to the bodily organ.

In at least one embodiment described herein, the medical device includes a controllable orienting means for adjusting the orientation of the energy transfer element with respect to the bodily organ.

In another embodiment, the medical device is collapsible into a collapsed configuration for insertion and removal through a surgical incision, and the medical device is expandable to a full configuration for attachment to a bodily organ.

In another embodiment, the medical device has a concave support element that is conformable to the shape of the bodily organ.

In at least one embodiment, the medical device includes a flexible membrane attached to the open face of the concave support element. This flexible membrane hermetically separates the enclosed space from the bodily organ when the medical device is attached to the bodily organ. The flexible membrane permits the bodily organ to protrude into the enclosed space when the fluid is at an operating pressure that is lower than the external pressure, thereby removably attaching the medical device to the bodily organ.

One example of an application of the present invention is removably attaching the medical device to the anterior surface of the liver of a patient, wherein the energy transfer element of the medical device transmits intense ultrasound energy to ablate a volume of diseased tissue within the liver.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

We specifically present the novel features of this invention in the appended claims. The reader may best understand, however, the organization and the methods of operation of this invention, by referring to the following description, taken in conjunction with the accompanying drawings.

FIG. 2A is an end view of an energy transfer element 102.

FIG. 2B is a side view of energy transfer element 102 attached to a cable 104.

FIG. 3A is an end view of a fluid filled balloon 106 containing energy transfer element 102 shown in FIG. 2B.

FIG. 3B is a side view of fluid filled balloon 106 containing energy transfer element 102 shown in FIG. 3A.

FIG. 4A is an end view of a first embodiment 100 of IUS device 30 shown in FIG. 1.

FIG. 4B is a side view of first embodiment 100 shown in FIG. 4A, and includes a concave support element 112 containing fluid filled balloon 106 and energy transfer element 102.

FIG. 5 is a sectional view taken at line 5—5 of first embodiment 100 shown in FIG. 4B.

FIG. 23 is a top view of a sixth embodiment 600 of IUS device 30 shown in FIG. 1, and includes a plurality of fluid chambers 614.

FIG. 24 is an end view of sixth embodiment 600 shown in FIG. 23.

FIG. 25 is a side view of sixth embodiment 600 shown in FIG. 23, shown in a straight position.

FIG. 26 is a side view of sixth embodiment 600 shown in FIG. 25, shown conformed to the shape of an organ 12.

DETAILED DESCRIPTION OF THE INVENTION

Before explaining the present invention in detail, it should be noted that the invention is not limited in its application or use to the details of construction and arrangement of parts illustrated in the accompanying drawings and description The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Figure 1:
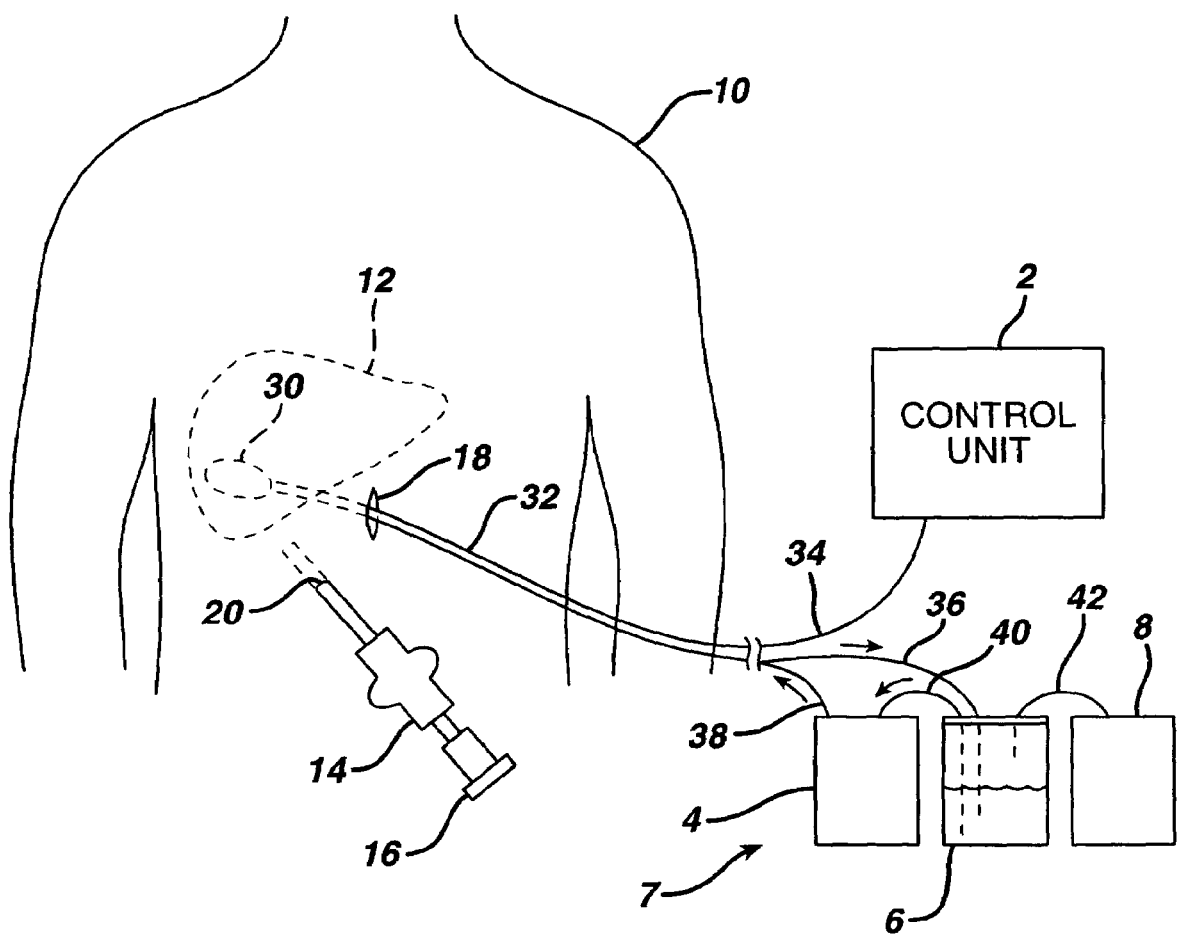
FIG. 1 is a schematic representation of an IUS device 30 introduced into a surgical patient 10 through an incision 18 and attached to an organ 12, with visualization through a laparoscope 16.

FIG. 1 is a schematic representation of the present invention, a medical device 30, as it may be used on a bodily organ 12 of a surgical patient 10. Medical device 30 preferably incorporates intense ultrasound energy and is therefore also referred to as an IUS device 30. IUS device 30 is not limited to open or endoscopic surgical procedures, but may also be used for external, non-invasive medical procedures as will be described. As shown in FIG. 1, the physician passes IUS device 30 through an incision 18. If desired, the physician may use a laparoscope 16 through a trocar port 14 at an entry point 20 of surgical patient 10 to facilitate placement of IUS device 30 on organ 12. For the example shown in FIG. 1, organ 12 is the liver.

A bundle 32 connects IUS device 30 to a control unit 2 and a fluid management system 7, which comprises a fluid pump 4, a fluid reservoir 6, and a vacuum source 8. A suitable fluid pump 4 is a Masterflex US Compact, Low-Flow, Variable Speed Drive Model No. 77200-00 coupled with a standard pump head Model No. 7016-21 having a flow capacity in the range of 2.1 to 560 ml/min. A suitable vacuum source 8 is an Air Cadet Vacuum Pressure Pump Model No. SD-07530-40 (−508 mm Hg max vacuum) available from Cole-Parmer Instrument Company. General purpose laboratory vinyl tubing having an inner diameter in the range of approximately 1.6 to 6.4 mm may be used for fluid interconnections of fluid management system 7. For the example in FIG. 1, fluid management system 7 is a closed system so that fluid pressure may be adjusted to be less than atmospheric pressure. The partial vacuum operating pressure provided by vacuum source 7 is approximately in the range of −10 to −200 mm Hg. Bundle 32 contains a control cable 34, a fluid supply line 38, and a fluid return line 36. Bundle 32 may be flexible and permitted to lay on top of the supine, draped patient, and perhaps taped to surgical patient 10 near incision 18. Segmental portions of bundle 32 may also be rigid or semi-rigid to aid the physician in placement of IUS device 30 on organ 12. The physician may also use readily available ancillary devices not shown to support and hold bundle 32 during the procedure, as long as IUS device 30 is permitted to move freely with the movement of organ 12. A fluid output line 40 fluidly connects fluid reservoir 6 to fluid pump 7. A vacuum line 42 fluidly connects vacuum source 8 to fluid reservoir 6.

In one embodiment of the present invention for which medical device 30 is an IUS device, control unit 2 of FIG. 1 controls the transmission of IUS energy from energy transfer element 102 and performs automated control of IUS focal depth and directivity. Control unit 2 generally comprises a function generator with operator-controlled activation, a power amplifier, and an electrical matching network. A suitable function generator is Hewlett Packard Corporation Model No. 33120A Function/Arbitrary Waveform Generator with input provided by a Wavetek 50 MHz Pulse/Function Generator Model No. 81. A suitable amplifier is the Amplifier Research Amplifier Model 150A 100A. Control unit 2 may also include conventional devices for transducer characterization and feedback measurement, such as a Thruline Wattmeter Model No. 4410A available from Bird Corporation, an Ultrasonic Power Meter Model UPM-DT-1 E available from Ohmic Instruments Company, a LeCroy LC534AL 1 GHz Oscilloscope, and a Hewlett Packard HP4194A Impedance/Gain-Phase Analyzer. Control unit 2 may further include a host personal computer with an IEEE-488 interface to allow program-based control of function generators and other clinical/laboratory apparatuses. The aforementioned devices are offered by way of example only; other devices or combinations of devices are well known by those skilled in the art for controlling the transmission of ultrasound energy from energy transfer element 102.

FIGS. 2A and 2B show a generic representation of an energy transfer element 102, which transmits energy from a face 103. For the embodiments disclosed herein, energy transfer element 102 transmits intense ultrasonic energy and has approximately a 10 mm square by 50 mm long cylindrical shape. The size and shape of energy transfer element 102, however, may vary significantly. Energy transfer element 102 may also have a circular or other cross sectional shape. Cable 104 electrically connects energy transfer element 102 to control unit 2 shown in FIG. 1. Cable 104 may comprise, for example, a single bundle containing a plurality of wires. Cable 104 may alternately comprise a plurality of separated wires or a ribbon cable containing a plurality of wires so that cable 104 is relatively flexible. Flexible, printed circuits may also be used in this application. Energy transfer element 102 contains one or more piezoelectric elements, which may be arranged in any one of the various arrays that are well known in the art. Energy transfer element 102 may also include various combinations of matching layers, absorptive layers, reflective layers, lens configurations, air gap layers, encapsulation materials, seals, and internal cooling, again as is well known in the art. Control unit 2 controls the transmission of IUS energy from energy transfer element 102 for treating tissue, but control unit 2 may also be used with energy transfer element 102 to image tissue or to monitor the progress of tissue treatment.

The present invention is not limited to the use of intense ultrasonic energy for treating tissue, but may also incorporate other energy modalities to accomplish other therapeutic or diagnostic effects. For example, energy transfer element 102 may comprise one or more radio frequency (RF) electrosurgical electrodes that are electrically connected to a conventional monopolar or bipolar RF generator. Medical device 30 then is a platform for holding the electrodes against tissue during highly controlled ablation. In another example, energy transfer element 102 comprises an electrically induced heat element for locally warming the underlying tissue. In another example, energy transfer element 102 may comprise an electromyography transducer for detecting electric potentials developed in underlying muscle tissue.

FIGS. 3A and 3B show energy transfer element 102 inside of a balloon 106 filled with a fluid 108. Balloon 106 may be made of an elastomer such as silicone rubber, for example, which is practically transparent to IUS energy. Balloon 106 may also be made of a thin-wall plastic such as PET so that balloon 106 assumes a predetermined shaped when pressurized with fluid 108. Fluid supply line 38 and return line 36, together with cable 104, pass through a sealed neck 110 of balloon 106. Fluid 108 may be water, saline, oil, or any one of the well-known IUS coupling fluids. Circulation of fluid 108 inside of balloon 106 also cools energy transfer element 102, thus maintaining the efficiency and life of energy transfer element 102 and protecting adjacent tissue.

FIGS. 4A, 4B, and 5 show views of an embodiment 100 of IUS device 30 in FIG. 1. Balloon 106 and energy transfer element 102 mount inside a concave support element 112 having an open side 113. Concave support element 112 includes a concave support element neck 114 that sealingly retains cable 104, fluid supply line 38, fluid return line 36, and a vacuum line 116 for creating a partial pneumatic vacuum inside a space 120 between balloon 106 and concave support element 112. Face 103 of energy transfer element 102 faces downward against organ 12 in order to transmit energy through open side 113 of concave support element 112. When vacuum line 116 is connected to vacuum source 8 (FIG. 1), embodiment 100 may be attached to organ 12 as shown in FIG. 5. The physician may use a surgical forceps or the like to hold onto a grasping pin 118 during positioning of embodiment 100 onto organ 12. Concave support element 112 may be made of a rigid, biocompatible material such as injection molded polycarbonate, or may also be made of a relatively flexible, biocompatible elastomer such as a molded polyurethane rubber. Optionally, cable 104 may be rotationally mounted in concave support element neck 114 and mechanically engaged to an external rotation apparatus such as a stepper motor (not shown) inside of control unit 2 (FIG. 1), thus comprising an orientation means. Energy transfer element 102 may then be rotated about its longitudinal axis within a limited arc sector (+/−45 degrees for example). Rotating energy transfer element 102, together with electronically moving the IUS energy beam within a plane that contains the longitudinal axis of energy transfer element 102 and is perpendicular to face 103, allows treatment of a volume of tissue in organ 12.

Figure 6:
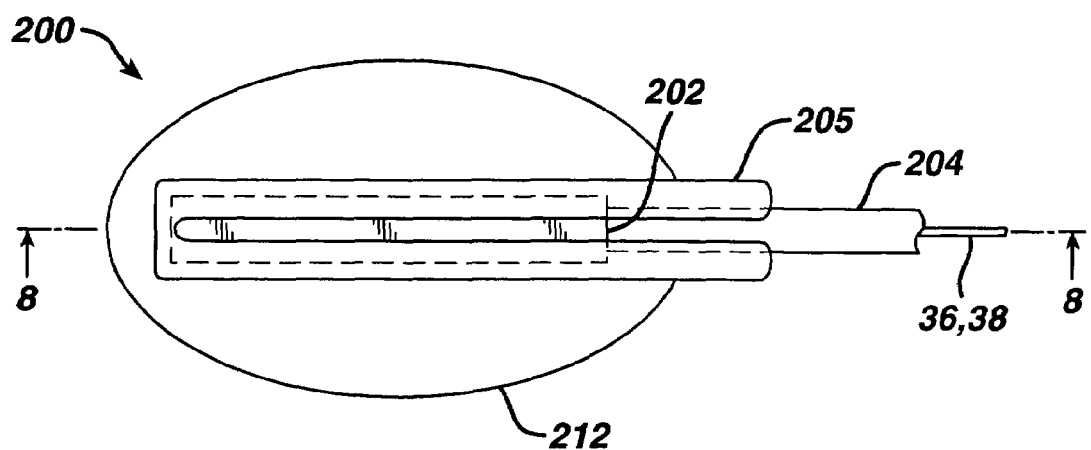
FIG. 6 is a top view of a second embodiment 200 of IUS device 30 shown in FIG. 1.
Figure 7:
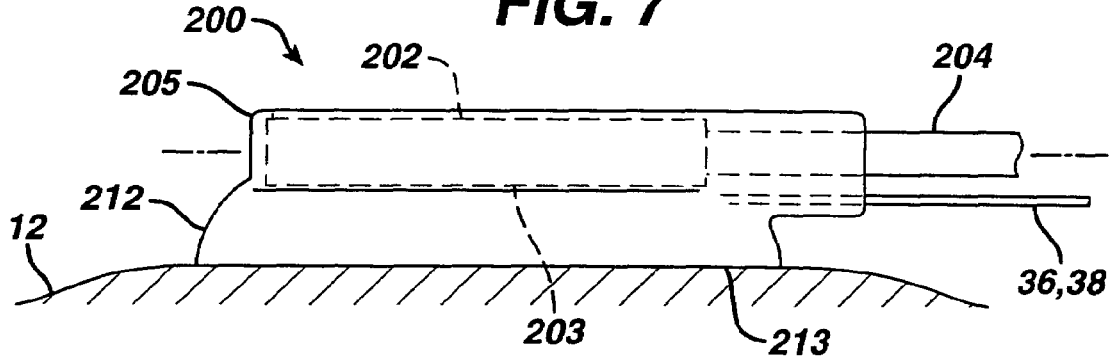
FIG. 7 is a side view of second embodiment 200 shown in FIG. 6.
Figure 8:
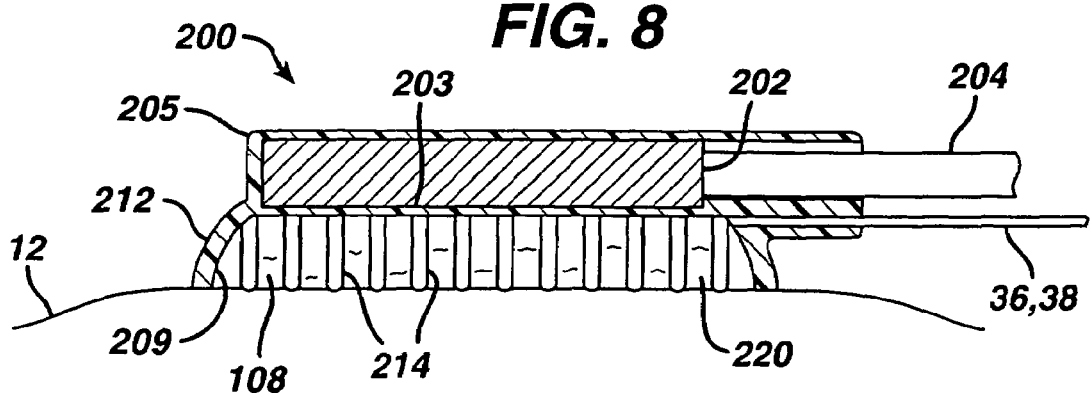
FIG. 8 is a sectional view taken at line 8—8 of second embodiment 200 of FIG. 6, and includes an energy transfer element 202 mounted in a concave support element 212 having a plurality of projections 214.

FIGS. 6–8 show an embodiment 200 of IUS device 30 of FIG. 1. Embodiment 200 comprises a concave support element 212, a energy transfer element 202 mounted within a energy transfer element enclosure 205 of concave support element 212 with a face 203 transmitting IUS energy toward an open side 213 that attaches to organ 12. Embodiment 200 further comprises a cable 204, fluid supply line 38, and fluid return line 36. A plurality of projections 214 extends from an inside surface 209 of concave support element 212 in a direction towards concave support element open side 213. Fluid supply line 38 and fluid return line 36 fluidly connect to fluid management system 7 depicted in FIG. 1. The operator positions embodiment 200 onto organ 12, thus defining a space 220 between concave support element 212 and organ 12. The operator then actuates fluid management system 7 to fill space 220 with fluid 108, purging all air from space 220. Once filled with fluid 108, a hydraulic vacuum within space 220 is created when vacuum source 8 of fluid management system 7 is actuated so that embodiment 200 attaches atraumatically to organ 12. Projections 214 prevent organ 12 from being drawn into space 220 and help to maintain communication of vacuum to the surface of organ 12 under concave support element 212. The operator may then actuate control unit 2 to activate energy transfer element 202 and begin treating the tissue. When treatment of the tissue stops, the operator or control unit 2 turns off the hydraulic vacuum and the operator removes embodiment 200 from organ 12. Concave support element 212 and energy transfer element enclosure 205 may be integrally molded as one piece from a variety of rigid or semi-rigid, biocompatible plastics or elastomers as described earlier. As shown for embodiment 200, energy transfer element enclosure 205 may easily be constructed so that energy transfer element 202 and cable 204 may be detached for cleaning, sterilization, and reuse on another patient. Concave support element 212, concave support element enclosure 205, fluid supply line 38, and fluid return line 36 are optionally disposable.

Figure 9:
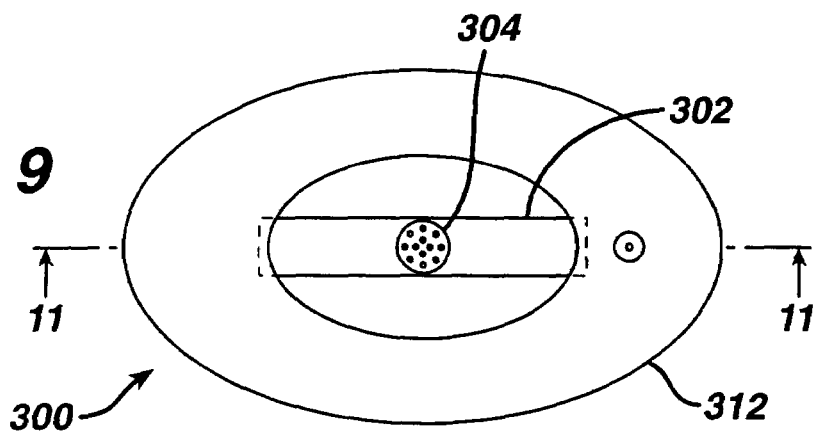
FIG. 9 is a top view of a third embodiment 300 of IUS device 30 shown in FIG. 1.
Figure 10:
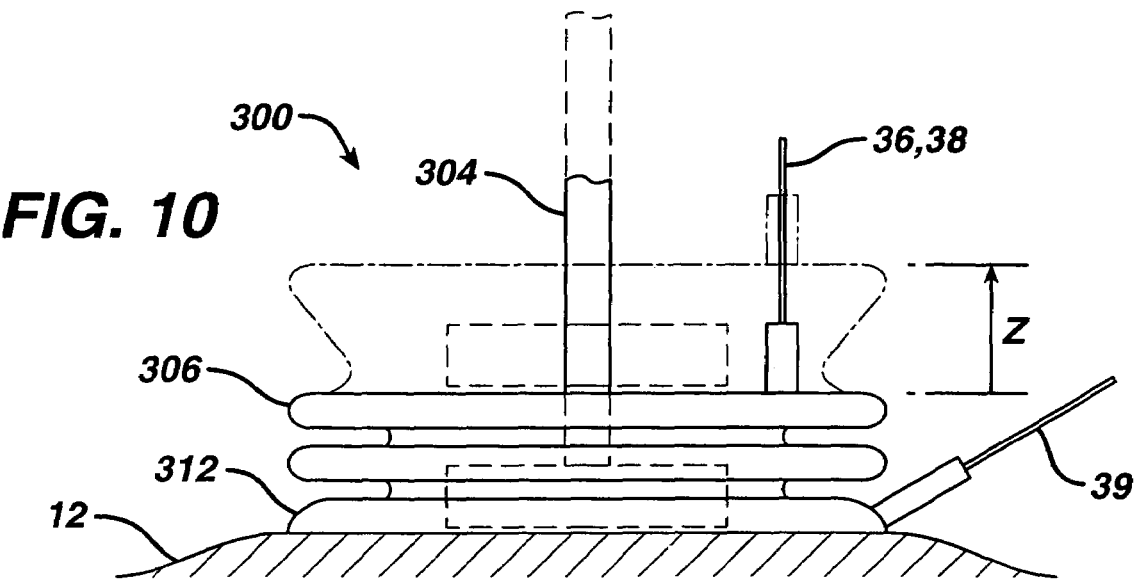
FIG. 10 is a side view of third embodiment 300 shown in FIG. 9, showing a bellows 306 vertically extendable by a distance Z.
Figure 11:
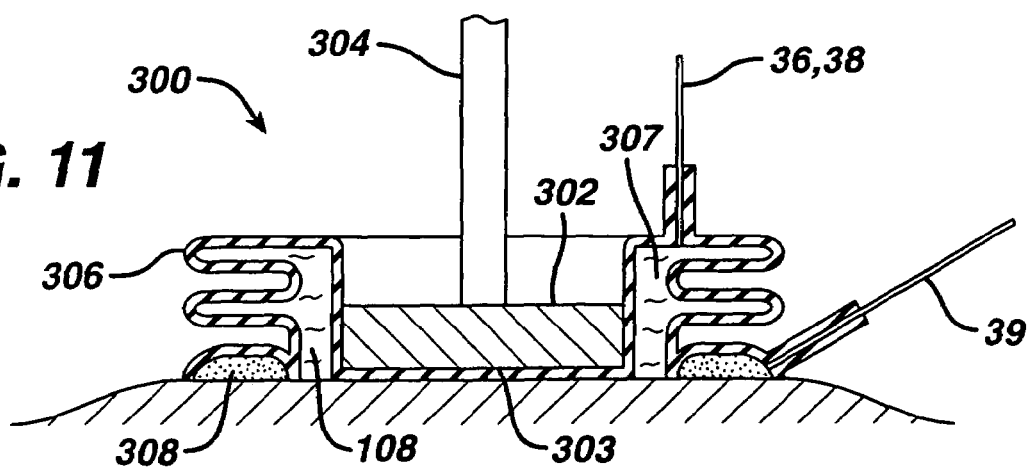
FIG. 11 is a sectional view of third embodiment 300 taken at line 11—11 in FIG. 9, and includes a volume 307 containing a fluid 108 and an annular chamber 308 connected to a vacuum source 39.
Figure 12:
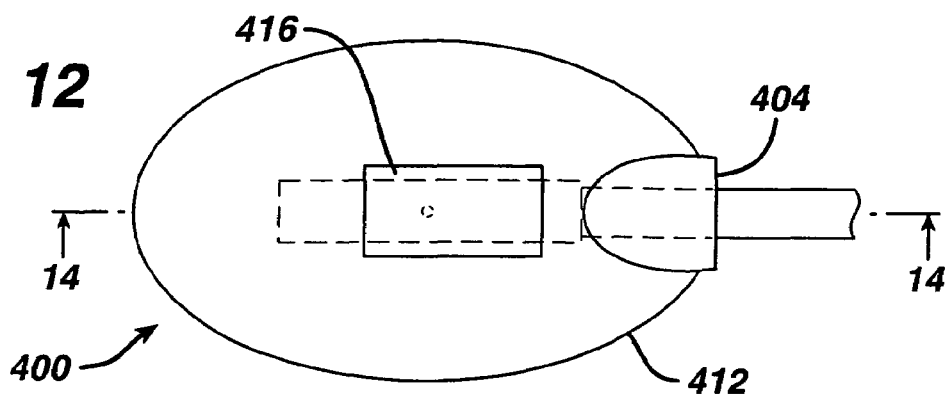
FIG. 12 is a top view of a fourth embodiment 400 of IUS device 30 shown in FIG. 1.
Figure 13:
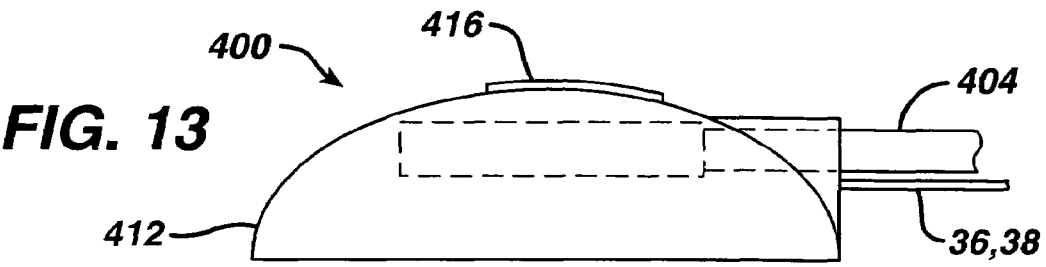
FIG. 13 is a side view of fourth embodiment 400 shown in FIG. 12.
Figure 14:
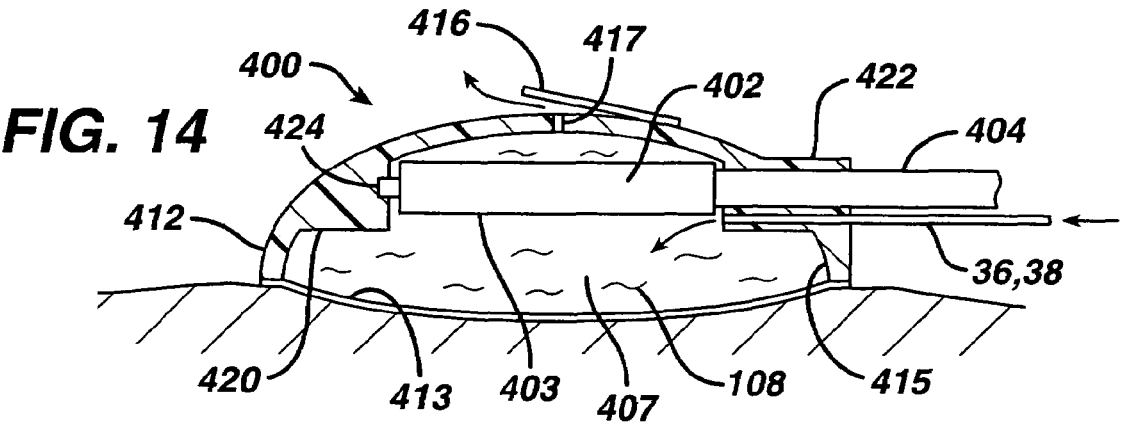
FIG. 14 is a sectional view of fourth embodiment 400 taken at line 14—14 of FIG. 12, and includes an energy transfer element 402 rotatably mounted in a concave support element 412 with a membrane 413, and also including a vent 417 open during the inflow of fluid 108.
Figure 15:
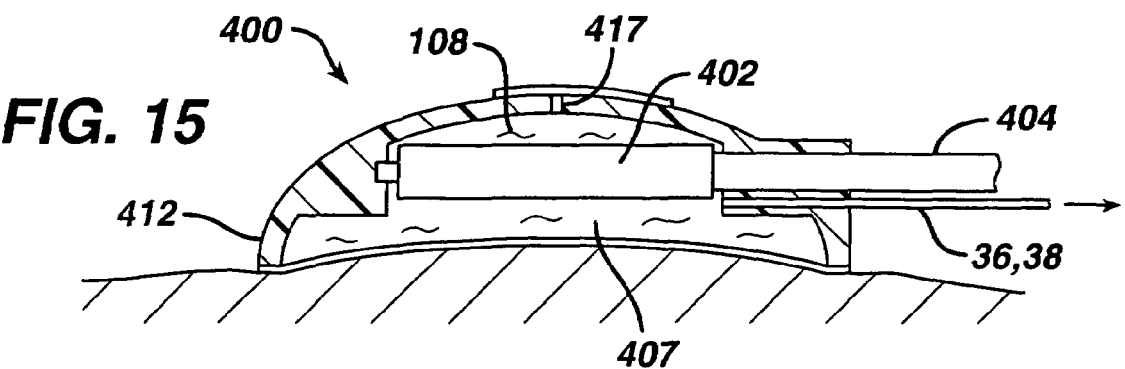
FIG. 15 is a sectional view of fourth embodiment 400 of FIG. 14, showing vent 417 closed as a hydraulic vacuum is applied to fluid 108.
Figure 16:
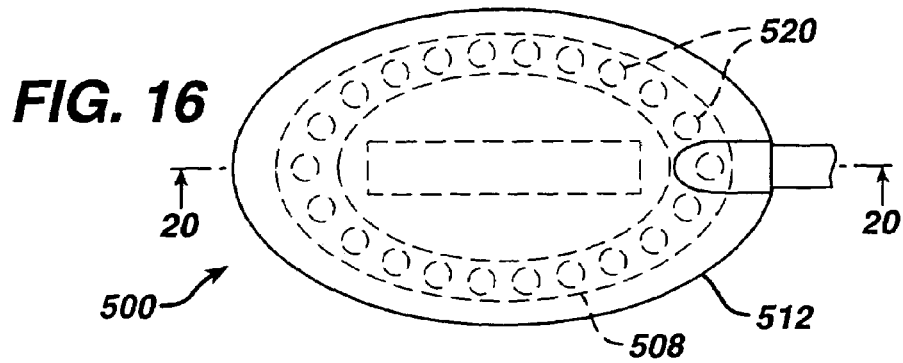
FIG. 16 is a top view of a fifth embodiment 500 of IUS device 30 of FIG. 1, and includes an inflatable housing 512.
Figure 17:
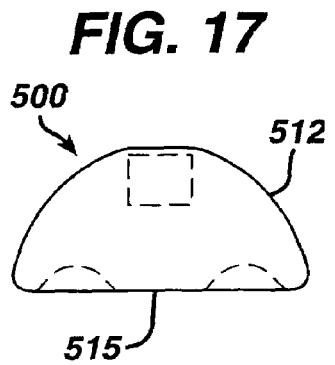
FIG. 17 is an end view of fifth embodiment 500 shown in FIG. 16.
Figure 18:
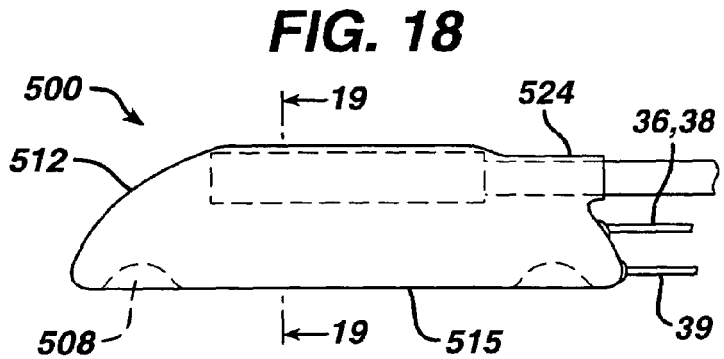
FIG. 18 is a side view of fifth embodiment 500 shown in FIG. 16.
Figure 19:
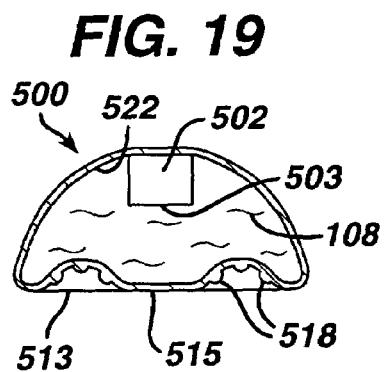
FIG. 19 is a sectional view of fifth embodiment 500 taken at line 19—19 of FIG. 18.
Figure 20:
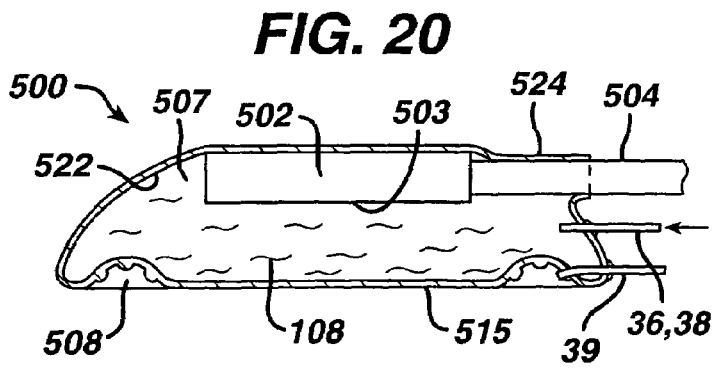
FIG. 20 is a sectional view of fifth embodiment 500 taken at line 20—20 of FIG. 16, and includes an annular chamber 508 connected to a vacuum line 39.
Figure 21:
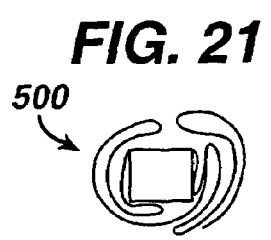
FIG. 21 is an end view of fifth embodiment 500 shown in a collapsed configuration.
Figure 22:
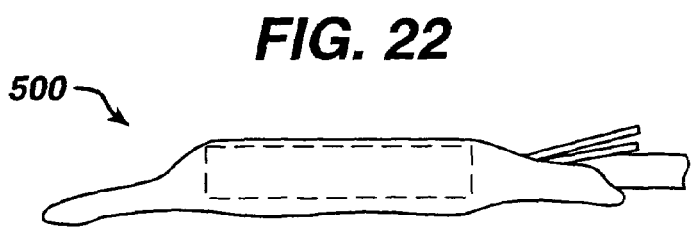
FIG. 22 is a side view of fifth embodiment 500 shown in a collapsed configuration.
Figure 27:
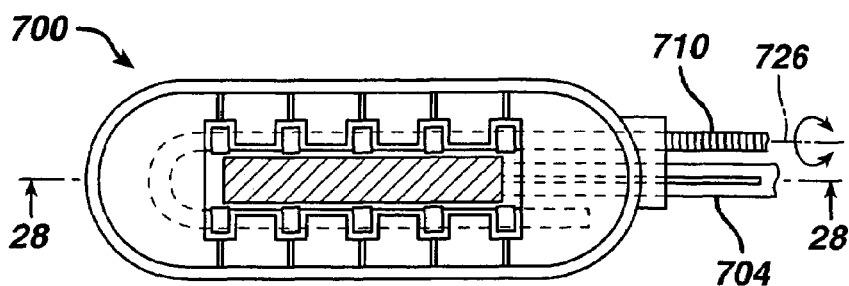
FIG. 27 is a bottom view of a seventh embodiment 700 of IUS device 30 shown in FIG. 1.
Figure 28:
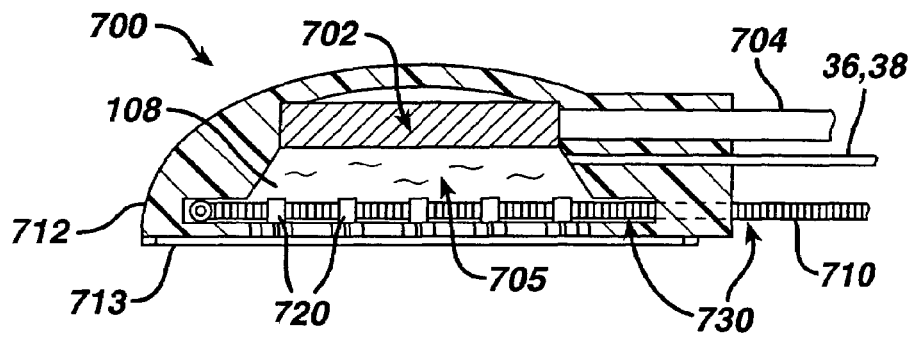
FIG. 28 is a sectional view taken at line 28—28 of seventh embodiment 700 shown in FIG. 27, and includes an actuation cable 710 for actuating a plurality of hook elements 720.
Figure 29:
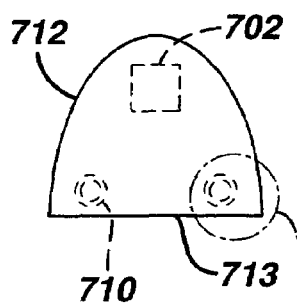
FIG. 29 is an end view of seventh embodiment 700 shown in FIG. 28.
Figure 30:
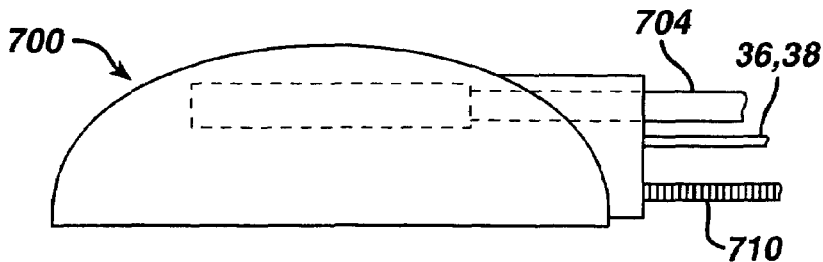
FIG. 30 is a side view of seventh embodiment 700.

FIGS. 9–11 show an embodiment 300 of IUS device 30 of FIG. 1. Embodiment 300 includes a positioning means that comprises a concave support element 312 having a bellows 306 that is extendable between a first position and a second position. This enables the operator to adjust vertically the distance between energy transfer element 302 (FIG. 11) and the tissue being treated.

The operator may use this mechanical positioning to center initially the focal point of IUS device 30 within the electronically adjustable range of IUS device 30. This facilitates treatment of diseased tissue located several centimeters deep in the organ as well as diseased tissue located just below the surface of the organ. A cable 304 extends from energy transfer element 102 in the same axis as the direction of extension of bellows 306.

Embodiment 300 further comprises a energy transfer element 302 mounted to bellows 306 so that a face 303 of energy transfer element 302 may be positioned next to organ 12 or spaced apart from organ 12 at a desired distance. In FIG. 10, "z" indicates movement of bellows 306 from the first position to the second position. When a first pressure is supplied to volume 307, bellows 306 extends to the first position as shown in FIG. 11. When a second pressure, which is greater than the first pressure, is supplied to volume 307, bellows 306 extends to the second position as shown by the phantom lines in FIG. 11. Intermediate positions are possible by variation of the pressure of fluid 108 between the first and second pressures. Embodiment 300 further comprises an annular chamber 308 that fluidly connects via vacuum line 39 to a pneumatic or hydraulic vacuum source for attaching embodiment 300 to organ 12. Fluid supply line 38 and fluid return line 36 maintain fluid flow in volume 307 for coupling and cooling energy transfer element 302, in addition to pressurizing bellows 306.

FIGS. 12–15 show an embodiment 400 of IUS device 30 of FIG. 1. Embodiment 400 comprises a concave support element 412, a cable 404 attached to a energy transfer element 402 having a face 403. Fluid supply line 38 and fluid return line 36 fluidly connect to fluid management system 7 depicted in FIG. 1. Embodiment 400 further comprises a valve 416 covering a vent 417, and a membrane 413 covering an opening 415 of concave support element 412. Concave support element 412 is preferably made of a rigid, biocompatible plastic or a semi-rigid, biocompatible elastomer as for the previous embodiments. Membrane 413 is made of a thin, elastic, fluid sealing material, such as silicone rubber, that is effectively transparent to the acoustic energy emitted by energy transfer element 402.

The operator positions embodiment 400 onto organ 12 over the tissue to be treated and actuates fluid system 7 to fill a fluid chamber 407 defined by concave support element 412 and membrane 413 with fluid 108. The pressure of the air or other fluids inside of fluid chamber 407 push open valve 416, which is normally closed, allowing the air or other fluids to escape through vent 417. Once fluid chamber 407 is filled with fluid 108, the operator may actuate fluid system 7 to create a hydraulic vacuum inside of fluid chamber 407 while firmly holding concave support element 412 against organ 12.

Organ 12 is drawn partway into fluid chamber 407 only to the extent permitted by the diaphragmatic resistance provided by membrane 413. In essence, membrane 413 behaves much like another thin tissue layer on organ 12, and the hydraulic vacuum inside of fluid chamber 407 causes embodiment 400 to attach to organ 12 atraumatically, while still containing fluid 108. Variation of the hydraulic vacuum pressure also allows adjustment of the distance between face 403 of energy transfer element 402 and organ 12. Embodiment 400 allows the operator the option of using a fluid media for fluid 108 that the operator prefers not to spill onto organ 12 and into the body cavity. This primarily helps to conserve fluid 108 (which may contain, for example, expensive therapeutic agents) and minimizes the need for aspirating fluid from the body cavity during the procedure. Embodiment 400 further includes a pivot block 420 projecting from concave support element 412 to support a post 424 extending from energy transfer element 402, and a neck 422 for rotationally supporting cable 404. Energy transfer element 402 may be pivoted about its longitudinal axis, either manually or under control of control unit 2 as described earlier, in order to sweep IUS energy through organ 12.

FIGS. 16–22 show an embodiment 500 of IUS device 30 of FIG. 1. Embodiment 500 comprises an inflatable housing 512, which has a full configuration (FIGS. 16–20) when an interior space 507 is filled with fluid 108, and which has a collapsed configuration (FIGS. 21–22) when fluid 108 and/or air have been evacuated from interior space 507. Fluid supply line 38 and fluid return line 36 communicate fluid under the desired pressure to fluid management system 7 shown in FIG. 1. When in the full configuration, embodiment 500 may be attached to organ 12 for treatment of tissue. When in the collapsed configuration, embodiment 500 may be easily passed through a minimally invasive incision in the abdominal wall of the patient, or through an appropriately sized trocar cannula, thus reducing postoperative pain and recovery time for the patient. Inflatable housing 512 may be molded, for example, from a tough and resiliently flexible, biocompatible polymer such as polyurethane or polyethylene. A energy transfer element 502 is attached, for example with an adhesive, to an interior surface 522 of inflatable housing 512, so that face 503 faces toward bottom side 515. A cable 504 exits through a tight-fitting, housing neck 524. Embodiment 500 further comprises an annular chamber 508 disposed on bottom side 515 of inflatable housing 512. Annular chamber 508 fluidly connects to a vacuum source by vacuum line 39. A membrane 513 covers annular chamber 508 and contains a plurality of ports 520 spaced apart over annular chamber 508. A multiplicity of bumps 518 on annular chamber 508 help to maintain vacuum communication within annular chamber 508. The operator positions embodiment 500 on organ 12 while inflatable housing 512 is inflated. The operator then may supply vacuum to annular chamber 508 to attach embodiment 500 to organ 12. Energy transfer element 502 may next be activated to treat tissue.

FIGS. 23–26 show an embodiment 600 of IUS device 30 of FIG. 1. Embodiment 600 is very similar to embodiment 200 shown in FIGS. 6–8, except that a concave support element 612 comprises a plurality of fluid chambers 614 that fluidly communicate via common lumen 613 and that may flex relative to each other. This allows a bottom surface 616 to become non-planar as shown in FIG. 26 so that embodiment 600 may easily conform to a curved portion of organ 12.

FIGS. 27–32 show an embodiment 700 of IUS device 30 of FIG. 1. Embodiment 700 is also very similar to embodiment 200 shown in FIGS. 6–8 except that an attachment mechanism 730 is provided to further facilitate attachment of embodiment 700 to organ 12. Embodiment 700 comprises a concave support element 712, a energy transfer element 702, a cable 704, fluid supply line 38, and fluid return line 36. Concave support element 712 has a bottom side 713 and a fluid chamber 705. Attachment mechanism 730 includes a plurality of hook elements 720 spaced apart and mounted on an actuation cable 710 that is rotatable about a curvilinear axis 726. Attachment mechanism 730 is outside the "field of view" of energy transfer element 702 so that energy transmitted from energy transfer element 702 to tissue passes only through fluid 108.

Figure 31:
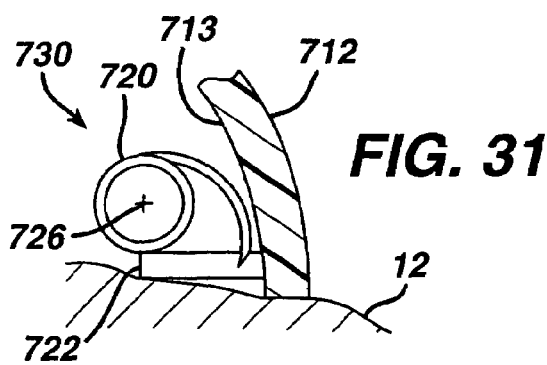
FIG. 31 is an enlarged, sectional view of a portion of seventh embodiment 700 of FIG. 29, showing hook element 720 in a retracted position.
Figure 32:
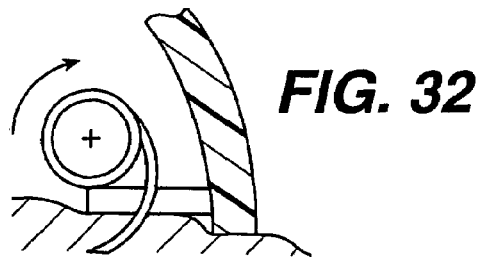
FIG. 32 shows hook element 720 of FIG. 31 in an extended position.

As shown in FIG. 31, hook elements 720 are retractable from tissue so that the operator may slide and position embodiment 700 on organ 12. A peripheral shelf 722 extending from an inside surface 713 of concave support element 712 supports hook elements 720. Once positioned, the operator uses a remotely located control (not shown) to rotate actuation cable 710 as shown in FIG. 32, thus rotating hook elements 720 simultaneously and penetrating the superficial tissue of organ 12. The hooks are approximately the same size, for example, as surgical vascular needles. The depth of penetration of the needles may be about in the range of 1–3 mm. Many more or less needles than shown may be used. Attachment mechanism 730 may be used alone or in combination with a hydraulic vacuum in fluid chamber 705 to attach embodiment 700 to organ 12. Laboratory experiments on live porcine liver show that bleeding from many tiny superficial punctures as created by hook elements 720 can be easily managed during the procedure.

Figure 33:
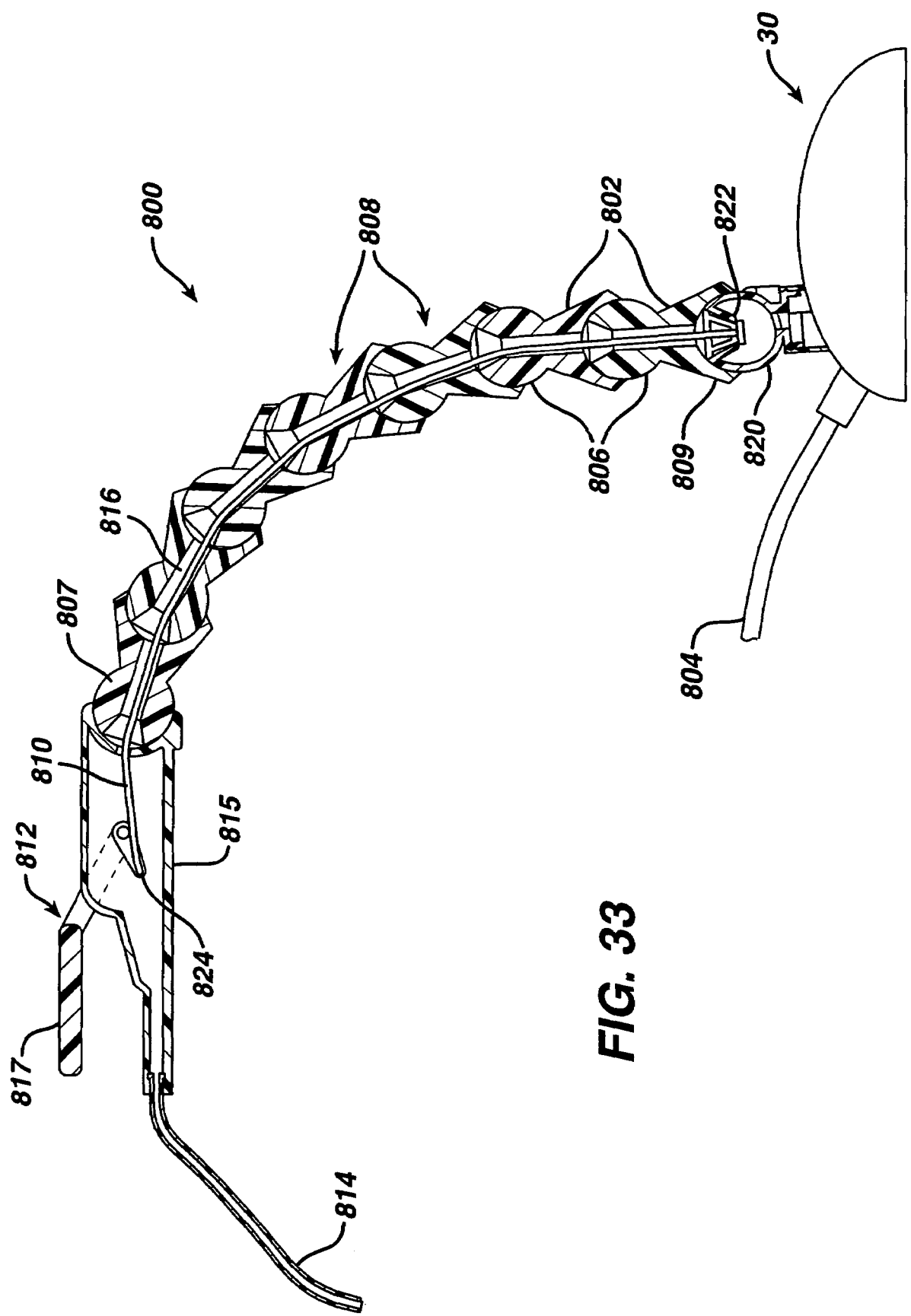
FIG. 33 is a sectional view taken at the curvilinear axis of a flexible shaft 800 attached to IUS device 30, wherein flexible shaft 800 includes a plurality of shaft elements 808 that are lockable into a fixed position.

FIG. 33 shows a flexible shaft 800 for holding IUS device 30 of FIG. 1. Flexible shaft 800 comprises a plurality of shaft elements 808, a tensioning element 810, a tensioning mechanism 812, a fluid line 814, and a cable 804. IUS device 30 may be embodied as any one of embodiments 200, 300, 400, 500, 600, and 700 described in the previous FIGS.

2–32. Each shaft element 808 has a ball 806 and a joining concave support element 802. Each ball 806 mates into joining concave support element 802 of adjacent shaft element 808 except for a proximal ball 807 that fits into a frame 815 of tensioning mechanism 812, and a distal joining concave support element 809 that fits onto a mount 820 attached to IUS device 30. Shaft elements 808 are retained to each other and to housing 815 and mount 820 by tensioning element 810 passing through a lumen 816. Lumen 816 fluidly connects to fluid line 814. Tensioning element 810 anchors to a retaining element 822 inside of mount 820. A proximal end 824 of tensioning element 810 attaches to a lever 817 of tensioning mechanism 812. When lever 817 is in a lock position, flexible shaft 800 rigidly assumes the configuration it is in. When lever 817 is in a release position, flexible shaft 800 is flexible. The operator may position IUS device 30 on an organ while using the rigid configuration of flexible shaft 800 as a handle. Once the operator attaches IUS device 30 to organ 12 via any one of the embodiments disclosed herein, the operator converts flexible shaft 800 to its flexible configuration so that movement of organ 12 is not significantly hindered.

The present invention effectively minimizes relative motion between an IUS energy transfer element and underlying tissue of the bodily organ, but may have applicability to other therapeutic or diagnostic energy modalities, including radio frequency electrosurgical energy, laser energy, conventional electrical heating elements, and others. Some of these energy modalities may be operable in a wireless mode, that is, without the need for electrical cables attached to the device, thus allowing the device to move even more freely with the movements of the organ. Further, the present invention has equal application in robotic-assisted surgical applications. In addition, the present invention may be useful for the administration of pharmaceutical agents or for the removal of fluids, toxins, or other substances from the patient. The present invention may be used for internal surgical procedures on various organs including the liver, stomach, and lungs, or may also be used externally and attached to the patient's skin to treat or diagnose underlying tissues.

We have shown numerous alternate embodiments of the present invention, but it will be obvious to those skilled in the art that such embodiments are only examples. Those skilled in the art will also realize numerous variations and substitutions without departing from the invention. We intend that the invention be limited only by the spirit and scope of the appended claims.

What is claimed is:

1. A medical device for use on a bodily organ of a patient, the medical device comprising:
    a) a support element defining a cavity and having an open portion that is removably attachable to the surface of the bodily organ, thereby defining an enclosed space adjacent to the bodily organ;
    b) an energy transfer element mounted to the support element, the energy transfer element positioned and oriented for transmitting energy directly to the bodily organ;
    c) a vacuum source fluidly connected to the enclosed space; and
    d) a plurality of hooks mounted on the support element for removably attaching the support element to the bodily organ.

2. The medical device of claim 1, wherein the enclosed space is fluidly connected to a fluid management system for circulating a fluid inside of the enclosed space.

3. The medical device of claim 1, wherein the support element further comprises an enclosure member containing a fluid and the energy transfer element and the energy transfer element transmits intense ultrasound energy in a frequency range of 1–30 megahertz, and the fluid acoustically couples the energy transfer element to the bodily organ.

4. The medical device of claim 1, wherein the vacuum source creates an operating pressure within the enclosed space that is lower than the pressure external to the support element.

5. The medical device of claim 1 further comprising positioning means for adjusting the position of the energy transfer element with respect to the bodily organ.

6. The medical device of claim 1, wherein the support element is conformable to the shape of the bodily organ.

* * * * *